(12) United States Patent
Wang et al.

(10) Patent No.: US 10,123,741 B2
(45) Date of Patent: Nov. 13, 2018

(54) CARDIAC CONDITION DETECTION

(71) Applicant: Huami Inc., Mountain View, CA (US)

(72) Inventors: Yuanxiang Wang, Mountain View, CA (US); Yuchen Wang, Mountain View, CA (US); Fei Wang, Mountain View, CA (US)

(73) Assignee: Huami Inc., Mountain View, CA (US)

( * ) Notice: Subject to any disclaimer, the term of this patent is extended or adjusted under 35 U.S.C. 154(b) by 58 days.

(21) Appl. No.: 15/364,743

(22) Filed: Nov. 30, 2016

(65) Prior Publication Data

US 2018/0146922 A1    May 31, 2018

(51) Int. Cl.
*A61B 5/0452* (2006.01)
*A61B 5/00* (2006.01)
(Continued)

(52) U.S. Cl.
CPC ............ *A61B 5/6804* (2013.01); *A41D 1/002* (2013.01); *A61B 5/0006* (2013.01); *A61B 5/0022* (2013.01); *A61B 5/0205* (2013.01); *A61B 5/0404* (2013.01); *A61B 5/044* (2013.01); *A61B 5/046* (2013.01); *A61B 5/04012* (2013.01); *A61B 5/0464* (2013.01); *A61B 5/04085* (2013.01); *A61B 5/04525* (2013.01); *A61B 5/11* (2013.01); *A61B 5/1102* (2013.01); *A61B 5/1117* (2013.01); *A61B 5/4836* (2013.01);
(Continued)

(58) Field of Classification Search
None
See application file for complete search history.

(56) References Cited

U.S. PATENT DOCUMENTS 7,130,681 B2    10/2006 Gebhardt et al.
8,140,154 B2 *   3/2012 Donnelly .......... A61B 5/02055
                                                 607/6
(Continued)

FOREIGN PATENT DOCUMENTS

CN     1933776 A    3/2007
CN   103126718 A    6/2013
(Continued)

OTHER PUBLICATIONS

"Accelerometer Placement for Posture Recognition and Fall Detection", H. Gjoreski et al, Intelligent Environment, 2011.
(Continued)

*Primary Examiner* — Kennedy Schaetzle
(74) *Attorney, Agent, or Firm* — Young Basile Hanlon & MacFarlane, P.C.

(57) ABSTRACT

Systems and methods for determining a cardiac condition of the human based on acceleration measurements received from one or more accelerometers of a garment worn by a human, electrocardiogram measurements received from electrodes of a garment worn by the human, and a machine learning model previously determined based on training data. An alert message that indicates the determined cardiac condition may be transmitted or displayed to the human wearing the garment or another person who will assist the human. For example, a posture pattern may be determined based on the acceleration measurements. The cardiac condition may be determined based in part on the posture pattern.

20 Claims, 10 Drawing Sheets

(51) Int. Cl.
*A41D 1/00* (2018.01)
*A61B 5/0205* (2006.01)
*A61B 5/04* (2006.01)
*A61B 5/0404* (2006.01)
*A61B 5/0408* (2006.01)
*A61B 5/044* (2006.01)
*A61B 5/046* (2006.01)
*A61B 5/0464* (2006.01)
*A61B 5/11* (2006.01)
*A61N 1/02* (2006.01)
*A61N 1/39* (2006.01)
*A61N 1/04* (2006.01)

(52) U.S. Cl.
CPC ............ *A61B 5/7264* (2013.01); *A61B 5/746* (2013.01); *A61B 5/747* (2013.01); *A61N 1/025* (2013.01); *A61N 1/046* (2013.01); *A61N 1/0484* (2013.01); *A61N 1/3987* (2013.01); *A61B 5/1116* (2013.01); *A61B 2562/0209* (2013.01); *A61B 2562/0219* (2013.01)

(56) References Cited

U.S. PATENT DOCUMENTS

| | | | |
|---|---|---|---|
| 9,026,200 B2 | 5/2015 | Nagata et al. | |
| 9,750,433 B2* | 9/2017 | Hu | A61B 5/1123 |
| 2002/0087088 A1 | 7/2002 | Brodnick | |
| 2005/0060001 A1* | 3/2005 | Singhal | A61N 1/37264 607/19 |
| 2007/0027388 A1* | 2/2007 | Chou | A61B 5/0002 600/393 |
| 2010/0179452 A1* | 7/2010 | Srinivasan | A61B 5/0002 600/595 |
| 2011/0066007 A1* | 3/2011 | Banet | A61B 5/0205 600/301 |
| 2011/0246144 A1* | 10/2011 | Tanaka | A61B 5/04012 703/2 |
| 2015/0094558 A1* | 4/2015 | Russell | A61B 5/688 600/391 |
| 2016/0074667 A1* | 3/2016 | Sullivan | A61N 1/0484 607/6 |
| 2016/0120470 A1* | 5/2016 | Bogdanovich | A61B 5/6804 340/870.07 |
| 2016/0135706 A1* | 5/2016 | Sullivan | A61B 5/0059 600/301 |
| 2017/0087371 A1* | 3/2017 | Freeman | A61N 1/3987 |
| 2017/0095212 A1* | 4/2017 | Albadawi | A61B 5/02416 |
| 2017/0143977 A1* | 5/2017 | Kaib | A41D 13/1281 |
| 2017/0249445 A1* | 8/2017 | Devries | G06F 19/3475 |
| 2017/0281097 A1* | 10/2017 | Thakur | A61B 5/746 |
| 2018/0014779 A1* | 1/2018 | Donnelly | A61B 5/02055 |
| 2018/0035919 A1* | 2/2018 | Koivisto | A61B 5/1102 |
| 2018/0064397 A1* | 3/2018 | Horikawa | A61B 5/721 |
| 2018/0067565 A1* | 3/2018 | Yuen | G06F 3/017 |

FOREIGN PATENT DOCUMENTS

| | | |
|---|---|---|
| CN | 103781404 A | 5/2014 |
| CN | 203662751 U | 6/2014 |
| CN | 204698545 U | 10/2015 |
| CN | 105832328 | 8/2016 |
| JP | 2002159458 A | 6/2002 |

OTHER PUBLICATIONS

"Evaluation of a Threshold-based Tri-Axial Accelerometer Fall Detection Algorithm", Bourke et al, Gait & Posture, 2007.

"Optimal Placement of Accelerometers for the Detection of Everyday Activities", Ian et al, Sensors, 2013.

"Preprocessing Techniques for Context Recognition from Accelerometer Data", Figo et al, Personal and Ubiquitous Computing, 2010.

* cited by examiner

CARDIAC CONDITION DETECTION

TECHNICAL FIELD

This disclosure relates to cardiac condition detection.

BACKGROUND

Wearable devices for fitness monitoring applications are becoming increasingly commonplace. These wearable devices may be used to measure certain vital signals, such as pulse, which may be indicative of heart rate, while also supporting a variety of other applications, such as tracking a user's exercise and fitness progress, check a user's emails or social media accounts, etc. Electrocardiogram systems are available in hospitals and other controlled medical settings for gathering and processing electrical signals from a human body which may be indicative of heart function and cardiac conditions.

SUMMARY

Disclosed herein are implementations of cardiac condition detection.

In a first aspect, the subject matter described in this specification can be embodied in systems that include a garment that includes a plurality of electrodes and one or more accelerometers. The systems may include a processing apparatus that is configured to receive acceleration measurements from the one or more accelerometers and receive electrocardiogram measurements from the plurality of electrodes. The processing apparatus may be configured to determine a cardiac condition of a human based on the acceleration measurements, the electrocardiogram measurements, and a machine learning model previously determined based on training data. The processing apparatus may be configured to transmit or display an alert message that indicates the determined cardiac condition.

In a second aspect, the subject matter described in this specification can be embodied in methods that include receiving acceleration measurements from one or more accelerometers of a garment worn by a human and receiving electrocardiogram measurements from electrodes of a garment worn by the human. The methods may include determining a cardiac condition of the human based on the acceleration measurements, the electrocardiogram measurements, and a machine learning model previously determined based on training data. The methods may include transmitting or displaying an alert message that indicates the determined cardiac condition.

In a third aspect, the subject matter described in this specification can be embodied in systems that include a processor, a network interface, and a memory storing instructions executable by the processor that upon execution by the processor cause the processor to perform operations including receiving acceleration measurements from one or more accelerometers of a garment worn by a human and receiving electrocardiogram measurements from electrodes of a garment worn by the human. The operations may include determining a cardiac condition of the human based on the acceleration measurements, the electrocardiogram measurements, and a machine learning model previously determined based on training data. The operations may include transmitting, via the network interface, an alert message that indicates the determined cardiac condition.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION

Figure 1:
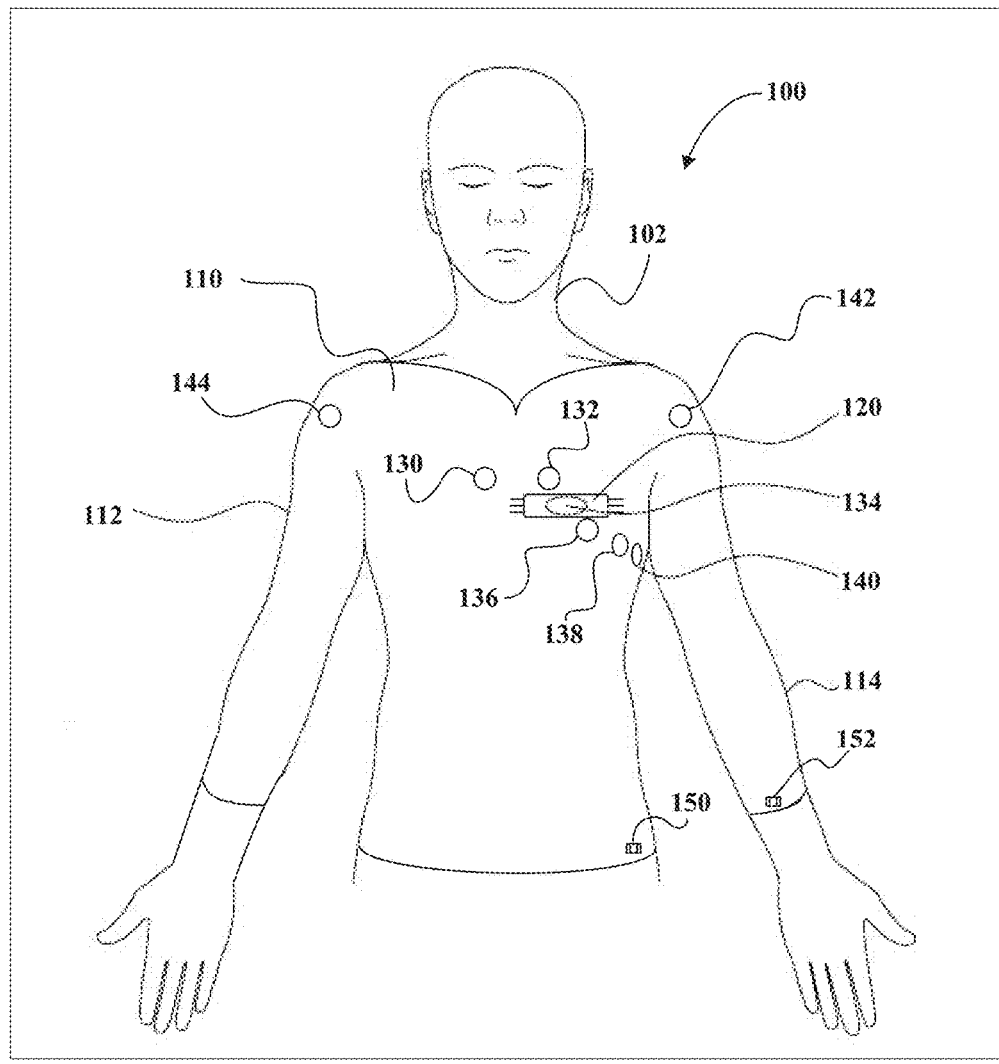
FIG. 1 illustrates an example garment for cardiac condition detection.

Cardiac function is an essential component of health and certain cardiac conditions (e.g., supraventricular tachycardia or ventricular fibrillation) can pose tremendous risks, even being life-threatening. Cardiac conditions can arise unexpectedly and when they do, time is of the essence. Fast detection and/or response to a cardiac condition can greatly improve outcomes for a person suffering from an adverse cardiac condition. However, it is not practical for a person, even a high-risk person, to live their life confined to controlled medical environments were conventional heart function monitoring can be performed. There is a need for solutions that provide fast and accurate detection of cardiac conditions in a variety of settings and circumstances a user encounters in their daily lives. Automatically detecting cardiac conditions in a variety of environments and circumstances (e.g., during different activities) presents many technical challenges.

Systems for cardiac condition detection including wearable devices are disclosed herein that addresses some of these technical challenges of automatically detecting cardiac conditions in a variety of circumstances. For example, a system for cardiac condition detection may include a garment that includes electrodes for detecting electrocardiogram measurements and/or accelerometers for detecting acceleration measurements. For example, one or more machine learning models may be used to classify features extracted from the electrocardiogram measurements and/or acceleration measurements and determine a cardiac condition of a human wearing the garment. In some implementations, machine learning models may be trained based on measurements captured using a garment regularly worn by a human. The posture pattern (e.g., sitting, walking, running, fallen) may be determined based on the acceleration measurements from the garment worn by the human. In some implementations, the determination of a cardiac condition may be based in part on a determined posture pattern for the human wearing the garment.

Quick action responsive to the detection of an adverse cardiac condition may be enabled. For example, alert messages indicating a cardiac condition of the human wearing the garment may be displayed and/or transmitted to alert the human, a health care provider, and/or a registered contact (e.g., friends and family) of the human to the occurrence of the cardiac condition. In some implementations, a defibrillator integrated in the garment may be automatically activated to apply first aid to the human in the event of certain emergency cardiac conditions (e.g., ventricular fibrillation).

In some implementations the identity of a human wearing the garment may be confirmed based on biometric features of the electrocardiogram measurements from the garment. Information associated with a confirmed identity of the human may be displayed or transmitted along with an alert message indicating an emergency cardiac condition to facilitate care for the human (e.g., when the human may have difficulty communicating because they are incapacitated).

Monitoring cardiac function for an individual over extensive periods of time and in a variety of different circumstances may also create new opportunities to discover detect patterns specific to that individual and track changes in cardiac function over time.

As used herein, the term "posture pattern" refers to a pattern of activity (e.g., motions and evolving postures) exhibited by a human that may be reflected in motion data for one or more parts of the human. Examples of posture patterns include sitting, standing, walking, running, exercising, lying, and fallen.

As used herein, the term "processing apparatus" refers to an apparatus including one or more processors that is configured to execute instructions to process data and/or to control peripheral components or devices.

FIG. 1 illustrates an example garment 100 for cardiac condition detection. The garment 100 may be configured to be worn by a human 102. The garment 100 may include electrodes, which may be used to measure electrical signals from the body of the human 102 when worn by the human 102. The garment 100 may include one or more accelerometers and/or other motion sensors (e.g., gyroscopes or magnetometers), which may be used to measure motion and/or orientation of the body of the human 102 when worn by the human 102. The garment 100 may include a material 110 (e.g., a fabric) configured to fit the body of a human and to fasten electrodes and/or motion sensors to the various positions on the body of the human 102. For example, the garment 100 may cover a portion of the chest of the human 102 when worn by the human 102. Posture patterns (e.g., sitting, walking, running, fallen) and/or cardiac conditions (e.g., supraventricular tachycardia or ventricular fibrillation) may be detected based on measurements collected with the sensors of the garment 100.

The example garment 100 includes a material 110 configured to be worn by the human 102 and to fasten electrodes and accelerometers to the various positions on the body of the human 102. For example, the material 110 may include cotton, flax, wool, ramie, silk, leather, polyester, nylon, spandex, and/or rayon. In some implementations, the material may have advantageous properties, such as being lightweight, stretchable, breathable, moisture-wicking, washable, and/or machine-washable. For example, the material 110 may be an electrical insulator. The example garment 100 is configured as a shirt, which covers portions of the torso of the human 102 and includes sleeves 112 and 114 that cover portions of the arms of the human 102.

The example garment 100, includes eight electrodes that may be fastened to positions on the body of the human 102 when the garment is worn. For example, the electrodes may be fastened in locations used for collecting medical grade electrocardiogram signals for analysis of cardiac condition. The example garment 100, includes the electrocardiogram sensor module 120, which may be electrically connected to the electrodes and detect voltage measurements from the electrodes for analysis and/or distribution (e.g., via wireless communications) to another processing apparatus (e.g., in a smartphone or a tablet) for analysis. The electrode 130 (e.g., V1) may be fastened at approximately the fourth intercostal space just to the right of the sternum of the human 102. The electrode 132 (e.g., V2) may be fastened at approximately the fourth intercostal space just to the left of the sternum of the human 102. The electrode 136 (e.g., V4) may be fastened at approximately the fifth intercostal space in the midclavicular line of the human 102. The electrode 134 (e.g., V3) may be fastened at approximately midway between the electrode 132 and the electrode 136 on the chest of the human 102. The electrode 138 (e.g., V5) may be fastened at approximately a position horizontally even with the electrode 136 along the left anterior axillary line of the human 102. The electrode 140 (e.g., V6) may be fastened at approximately a position horizontally even with the electrode 136 along the left midaxillary line of the human 102. The electrode 142 (e.g., LA) may be fastened at a position on the left arm of the human 102. The electrode 144 (e.g., RA) may be fastened at a position on the right arm of the human 102, approximately symmetric with the position of the electrode 142. For example, the electrodes (130, 132, 134, 136, 138, 140, 142, 144) may include an electrically conductive electrolyte gel and a conductor (e.g., silver or silver chloride). In some implementations, the electrodes (130, 132, 134, 136, 138, 140, 142, 144) are connected via conductors (e.g., wires) to the electrocardiogram sensor module 120. For example, conductors (not explicitly shown in FIG. 1) may be integrated (e.g., woven) into the material 110 to electrically connect the electrodes (130, 132, 134, 136, 138, 140, 142, 144) with the electrocardiogram sensor module 120.

The electrocardiogram sensor module 120 may include a wireless communications interface (e.g., a Bluetooth interface, ZigBee interface, or a WiFi interface). In some implementations, the electrocardiogram sensor module 120 may transmit electrocardiogram measurements from the electrodes (130, 132, 134, 136, 138, 140, 142, 144) to a processing apparatus (e.g., in a smartphone, tablet, or other computing device), which may in turn analyze and/or forward the electrocardiogram measurements. In some implementations, the electrocardiogram sensor module 120 may be integrated with a processing apparatus (e.g., a microprocessor of a microcontroller) that is attached to the garment 100 and configured to analyze the electrocardiogram signals in accordance with techniques described in this disclosure (e.g., the technique 400 of FIG. 4). For example, in response to analyzing the electrocardiogram measurements and detecting a cardiac condition, an integrated processing apparatus may utilize a wireless communications interface (e.g., a Bluetooth interface, ZigBee interface, or a WiFi interface) to transmit an alert message to another device (e.g., a smartphone, a tablet, or a wireless router).

The electrocardiogram sensor module 120 may be fastened to the chest of the human 102 when the garment 100 is worn. The electrocardiogram sensor module 120 may also include one or more accelerometers (e.g., a tri-axial accelerometer) that are fastened to the chest of the human 102 when the garment 100 is worn. For example, the electrocardiogram sensor module 120 may be integrated with a motion sensor module that includes, for example, an accelerometer, a gyroscope, and/or a magnetometer. For example, acceleration measurements from the accelerometer may be analyzed by a processing apparatus that is integrated with the electrocardiogram sensor module 120 or the acceleration measurements may be transmitted to another processing apparatus (e.g., in a smartphone or a tablet) for analysis.

The example garment 100 includes the motion sensor module 150 that is fastened to the waist of the human 102 when the garment 100 is worn. The motion sensor module 150 may include one or more accelerometers (e.g., a tri-axial accelerometer) that is fastened to the waist of the human 102 when the garment 100 is worn for measuring motion and/or orientation of the waist of the human 102. The motion sensor module 150 may include other motion sensors, such as a gyroscope or a magnetometer.

The example garment 100 includes the motion sensor module 152 that is fastened to a wrist or forearm of the human 102 when the garment 100 is worn. The motion sensor module 152 may include one or more accelerometers (e.g., a tri-axial accelerometer) that is fastened to a wrist of the human 102 when the garment 100 is worn for measuring motion and/or orientation of the wrist or forearm of the human 102. The motion sensor module 152 may include other motion sensors, such as a gyroscope or a magnetometer.

In some implementations, the garment 100 includes conductors (e.g., wires) that connect a processing apparatus (e.g., a microprocessor integrated with the electrocardiogram sensor module 120) to the motion sensor modules 150 and 152. For example, acceleration measurements from an accelerometer in the motion sensor module 150 may be received by a processing apparatus via the conductors. In some implementations, the motion sensor module 150 (and/or 152) includes a wireless interface (e.g., a Bluetooth interface, ZigBee interface, or a WiFi interface) and acceleration measurements from an accelerometer in the motion sensor module 150 (and/or 152) may be received by a processing apparatus via wireless communications with the motion sensor module 150 (and/or 152).

In some implementations (not shown in FIG. 1), a garment may cover additional portions of a human body and include electrodes and/or motion sensors (e.g., accelerometers) that are fastened at other positions on a human body when the garment is worn. For example, a garment may include leggings and electrodes fastened in symmetric position on the on the legs of a human when the garment is worn. For example, a garment may include sensor modules that are fastened on a lower back, hip, thigh, and/or foot of a human when the garment is worn.

In some implementations (not shown in FIG. 1), a garment may include a defibrillator, which may be activated by a processing apparatus responsive to a determination of the cardiac condition (e.g., ventricular fibrillation).

Figure 2:
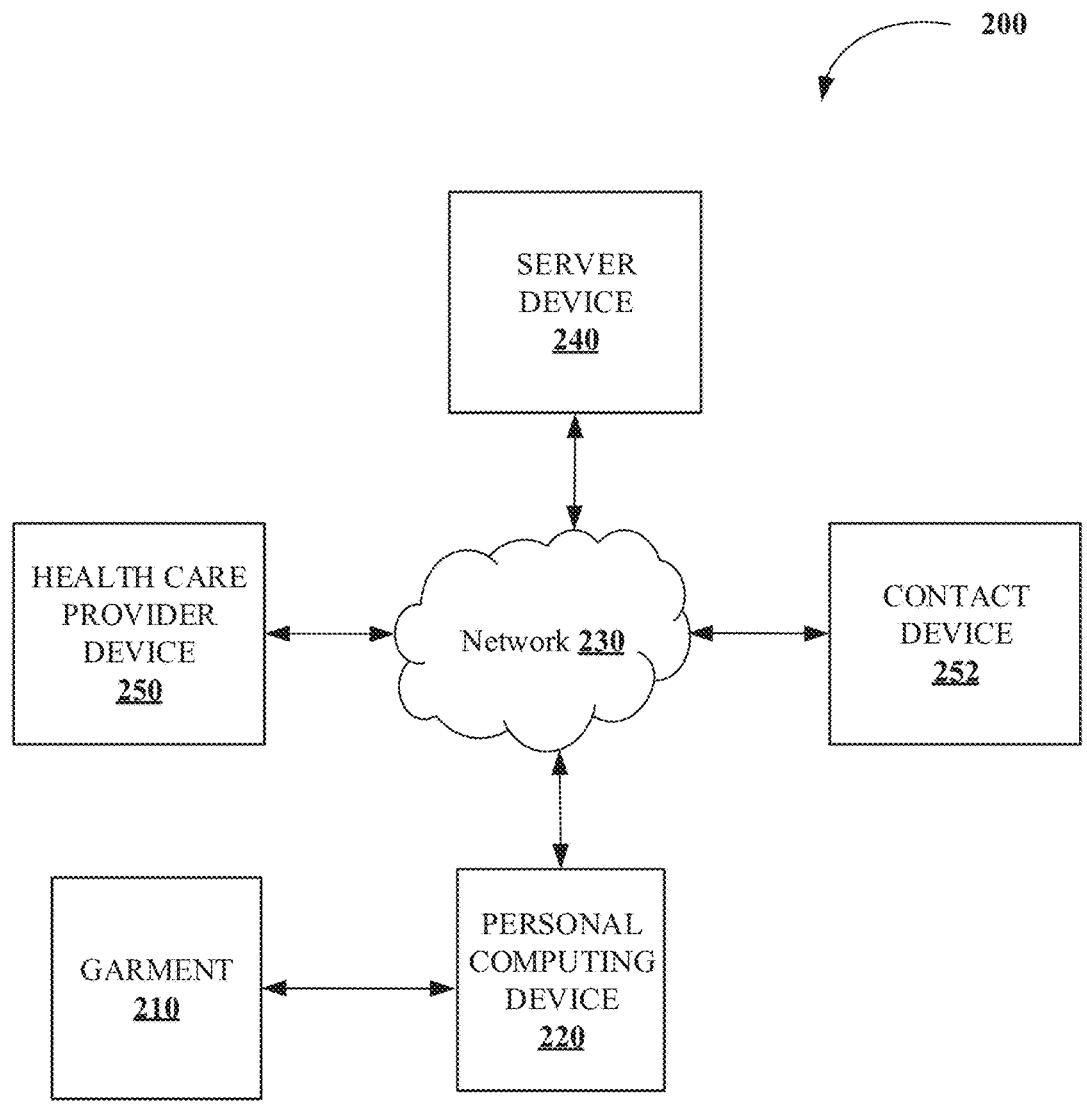
FIG. 2 is black diagram of an example system for cardiac condition detection.

FIG. 2 is black diagram of an example system 200 for cardiac condition detection. The system 200 includes a garment 210 (e.g., the garment 100 of FIG. 1) that includes electrodes and one or more accelerometers that are fastened to positions on a human body when the garment 210 is worn by the human.

The garment 210 may be in communication with the personal computing device 220 (e.g., a smartphone, a tablet, a laptop, a desktop computer, or a wireless router) to forward electrocardiogram measurements from the electrodes and acceleration measurements from the accelerometer(s) and/or to forward alert messages that are based on analysis of the electrocardiogram measurements and the acceleration measurements. For example, communication between the garment and the personal computing device may be accomplished using a wireless communications interface (e.g., a Bluetooth interface, ZigBee interface, or a WiFi interface). In some implementations, electrocardiogram measurements from the electrodes and acceleration measurements from the accelerometer(s) of the garment 210 may be forwarded to a processing apparatus in the personal computing device 220 for analysis using techniques disclosed herein (e.g., the technique 400 of FIG. 4).

The example system 200 also includes a server device 240, which may be accessed via the network 230 (e.g., a wide-area network such as the Internet). In some implementations, electrocardiogram measurements from the electrodes and acceleration measurements from the accelerometer(s) of the garment 210 may be forwarded to a processing apparatus in the server device 240 for analysis using techniques disclosed herein (e.g., the technique 400 of FIG. 4). For example, an alert indicating a cardiac condition of a human wearing the garment 210 may be generated, based on the electrocardiogram measurements from the electrodes and acceleration measurements from the accelerometer(s), by a processing apparatus in the server device 240 and sent to the personal computing device 220, the health care provider device 250, and/or the contact device 252 via the network 230. For example, an alert generated by the server device 240 may be forwarded to the garment and may cause a defibrillator integrated with the garment 210 to be activated (e.g., where the alert indicates a ventricular fibrillation condition has been detected for the human wearing the garment 210).

For example, the health care provider device 250 may be a computer operated by a hospital or doctor that regular treats the human wearing the garment 210 as a patient. For example, the contact device 252 may be a personal computing device of a friend or relative of the human wearing the garment 210 that has been registered to receive alerts about health of the human.

Figure 3A:
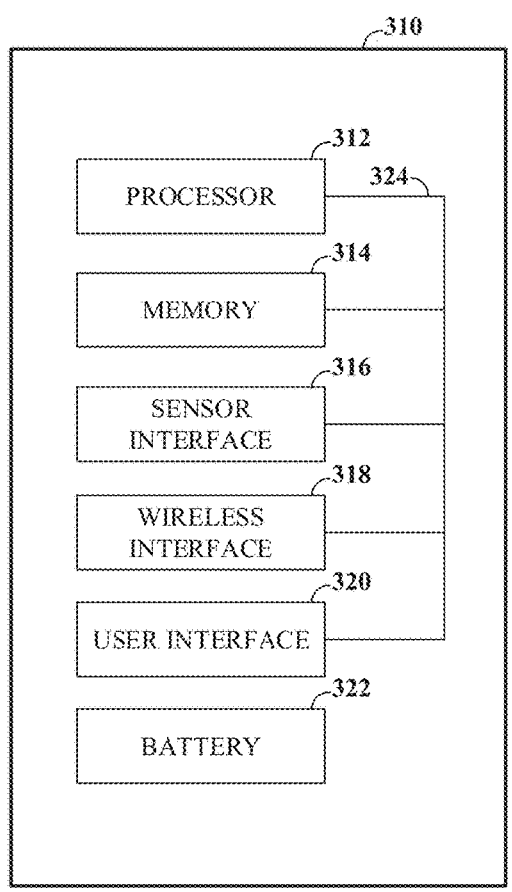
FIG. 3A is a block diagram of an example processing apparatus used for cardiac condition detection.

FIG. 3A is a block diagram of an example processing apparatus 310 used for cardiac condition detection. For example, processing apparatus 310 may be included in a garment (e.g., the garment 100 or the garment 210). The processing apparatus 310 may be used to implement techniques described in this disclosure (e.g., the techniques described in relation to FIGS. 4-9B). The example processing apparatus 310 includes a processor 312, a memory 314, a sensor interface 316, a wireless interface 318, a user interface 320, and a battery 322.

The processor 312 may include single or multiple processors each having single or multiple processing cores.

Alternatively, the processor 312 may include another type of device, or multiple devices, capable of manipulating or processing data.

The memory 314 may include random access memory device (RAM), flash memory, or any other suitable type of storage device such as a non-transitory computer readable memory. The memory 314 may include executable instructions and data that can be accessed by the processor 312. The memory 314 may include one or more DRAM modules such as double data rate synchronous dynamic random-access memory (DDR SDRAM). The memory 314 may include another type of device, or multiple devices, capable of storing data for retrieval or processing by the processor 312. The processor 312 may access and manipulate data in stored in the memory 314 via a bus 324.

The processing apparatus 310 may include a sensor interface 316, which may receive measurements from one or more sensors (e.g., electrocardiogram measurements, acceleration measurements, or angular rate measurements). In some implementations, the sensor interface 316 may implement a serial port protocol (e.g., I2C or SPI) for communications with sensor devices over conductors. In some implementations, the sensor interface 316 may include a wireless interface for communicating with one or more sensor modules via low-power, short-range communications (e.g., using a body area network protocol).

The processing apparatus 310 may include a wireless interface 318, which may enable wireless communications with a personal computing device (e.g., the personal computing device 220). For example, the wireless interface 318 may be used to forward measurements from sensors and/or information (e.g., alerts) based on analysis of measurements from sensors. For example, the wireless interface 318 may include a Bluetooth interface, a ZigBee interface, and/or a WiFi interface.

The processing apparatus 310 may include a user interface 320. For example, the user interface 320 may include an LCD display for presenting alerts or other messages to a human wearing a garment (e.g., the garment 100 or the garment 210) or another person assisting that human. For example, the user interface 320 may include button or switch enabling a person to manually turn the processing apparatus on and off.

The processing apparatus 310 may include a battery 322 that powers the processing apparatus and/or its peripherals. For example, the battery 322 may be charged wirelessly or through a micro-USB interface.

Figure 3B:
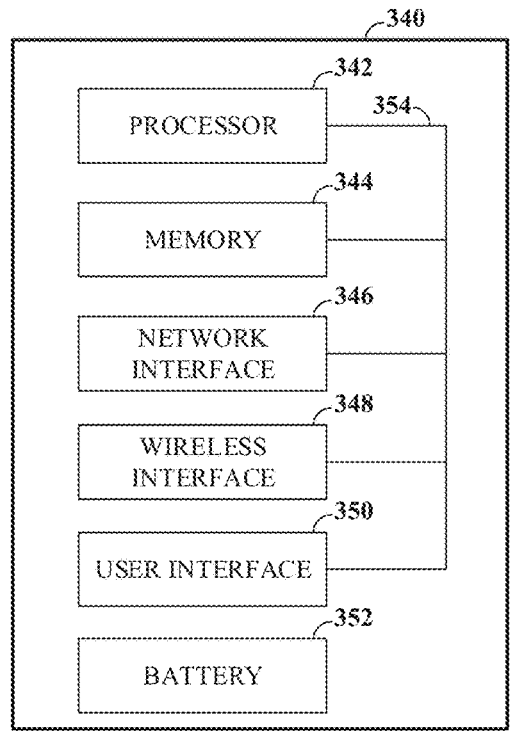
FIG. 3B is a block diagram of an example processing apparatus used for cardiac condition detection.

FIG. 3B is a block diagram of an example processing apparatus 340 used for cardiac condition detection. For example, processing apparatus 340 may be included in a personal computing device (e.g., the personal computing device 220). The processing apparatus 340 may be used to implement techniques described in this disclosure (e.g., the techniques described in relation to FIGS. 4-9B). The example processing apparatus 340 includes a processor 342, a memory 344, a network interface 346, a wireless interface 348, a user interface 350, and a battery 352.

The processor 342 may include single or multiple processors each having single or multiple processing cores. Alternatively, the processor 342 may include another type of device, or multiple devices, capable of manipulating or processing data.

The memory 344 may include random access memory device (RAM), flash memory, a read-only memory device (ROM), an optical disc, a magnetic disc, or any other suitable type of storage device such as a non-transitory computer readable memory. The memory 344 may include executable instructions and data that can be accessed by the processor 342. The memory 344 may include one or more DRAM modules such as double data rate synchronous dynamic random-access memory (DDR SDRAM). The memory 344 may include another type of device, or multiple devices, capable of storing data for retrieval or processing by the processor 342. The processor 342 may access and manipulate data in stored in the memory 344 via a bus 354.

The processing apparatus 340 may include a network interface 346, which may be used to transmit and receive data via a wired and/or wireless computing network (e.g., a cellular data network, a WiFi wireless LAN, an Ethernet LAN, and/or a WAN, such as the Internet). In some implementations, the network interface 346 may implement a network protocols (e.g., IPv4 or IPv6) for communications with other computing devices via a network.

The processing apparatus 340 may include a wireless interface 348, which may enable wireless communications with a peripheral device (e.g., the garment 100 or the garment 210). For example, the wireless interface 348 may be used to receive electrocardiogram measurements from electrodes and/or acceleration measurements from accelerometers of a garment (e.g., via transmissions from a wireless interface in a sensor module of the garment). In some implementations, the wireless interface 348 may be used to receive information (e.g., alerts), based on analysis of electrocardiogram and/or acceleration measurements from sensors, from a garment. For example, the wireless interface 348 may include a Bluetooth interface, a ZigBee interface, and/or a WiFi interface.

The processing apparatus 340 may include a user interface 350. For example, the user interface 350 may include a touchscreen display for presenting alerts or other messages to a human wearing a garment (e.g., the garment 100 or the garment 210) or another person assisting that human and detecting control gestures by a user. For example, the user interface 350 may include buttons or switches enabling a person to manually turn the processing apparatus on and off, adjust sound volume, etc. In some implementations, the user interface 350 may include a LCD display or CRT monitor for presenting alerts or other messages to a human wearing a garment (e.g., the garment 100 or the garment 210) or another person assisting that human and detecting control gestures by a user. In some implementations, the user interface 350 may include a keyboard, mouse, trackpad, and/or microphone for receiving user input.

The processing apparatus 340 may include a battery 352 that powers the processing apparatus and/or its peripherals. For example, the battery 352 may be charged wirelessly, through a micro-USB interface, or through a AC (alternating current) adapter cable.

Figure 3C:
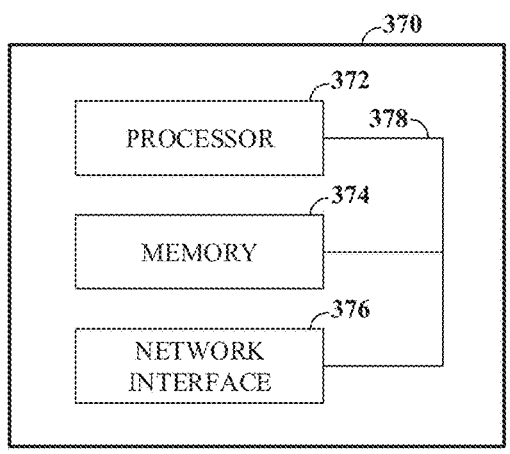
FIG. 3C is a block diagram of an example processing apparatus used for cardiac condition detection.

FIG. 3C is a block diagram of an example processing apparatus 370 used for cardiac condition detection. For example, processing apparatus 370 may be included in a server device (e.g., the server device 240). The processing apparatus 370 may be used to implement techniques described in this disclosure (e.g., the techniques described in relation to FIGS. 4-9B). The example processing apparatus 370 includes a processor 372, a memory 374, and a network interface 376.

The processor 372 may include single or multiple processors each having single or multiple processing cores. Alternatively, the processor 372 may include another type of device, or multiple devices, capable of manipulating or processing data.

The memory 374 may include random access memory device (RAM), flash memory, a read-only memory device (ROM), an optical disc, a magnetic disc, or any other suitable type of storage device such as a non-transitory computer readable memory. The memory 374 may include executable instructions and data that can be accessed by the processor 372. The memory 374 may include one or more DRAM modules such as double data rate synchronous dynamic random-access memory (DDR SDRAM). The memory 374 may include another type of device, or multiple devices, capable of storing data for retrieval or processing by the processor 372. For example, the memory 374 can be distributed across multiple machines or devices such as network-based memory or memory in multiple machines performing operations that can be described herein as being performed using a single computing device for ease of explanation. The processor 372 may access and manipulate data in stored in the memory 374 via a bus 378 or via computing network communications (e.g., where the memory includes a database server in separated from the processor 372 by a computing network).

The processing apparatus 370 may include a network interface 376, which may be used to transmit and receive data via a wired and/or wireless computing network (e.g., a cellular data network, a WiFi wireless LAN, an Ethernet LAN, and/or a WAN, such as the Internet). In some implementations, the network interface 346 may implement a network protocols (e.g., IPv4 or IPv6) for communications with other computing devices via a network. For example, electrocardiogram measurements from the electrodes of a garment (e.g., the garment 100 or the garment 210) may be received by the processing apparatus 370 via the network interface 376. For example, acceleration measurements from the accelerometers of a garment (e.g., the garment 100 or the garment 210) may be received by the processing apparatus 370 via the network interface 376. For example, information (e.g., an alert message) indicating a cardiac condition and/or a posture pattern may be transmitted by the processing apparatus 370 via the network interface 376 to another device registered to receive alerts (e.g., the health care provider device 250, the personal computing device 220, the garment 210, and/or the contact device 252.

Figure 4:
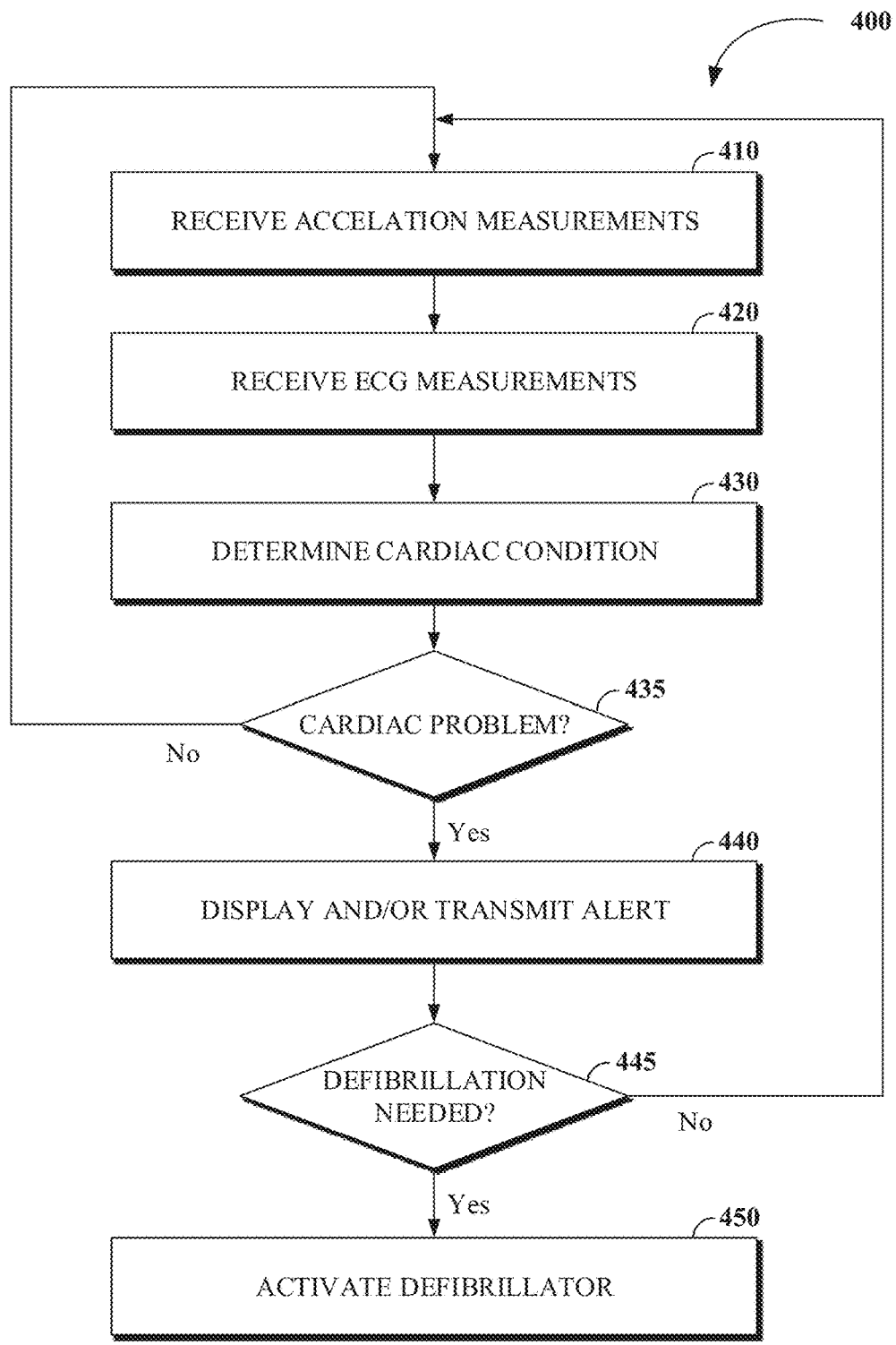
FIG. 4 is a flowchart of an example technique for cardiac condition detection.

FIG. 4 is a flowchart of an example technique 400 for cardiac condition detection. The technique 400 may include receiving 410 acceleration measurements from the one or more accelerometers of a garment worn by a human, receiving 420 electrocardiogram measurements from electrodes of a garment worn by the human, determining 430 a cardiac condition of the human based on the acceleration measurements and the electrocardiogram measurements, and transmitting or displaying 440 an alert message that indicates the determined cardiac condition. The technique 400 may be implemented by a processing apparatus (e.g., the processing apparatuses 310, 340, and 370) that is incorporated in or (directly or indirectly) in communication with the garment worn by the human. In some implementations, the technique 400 may be applied repeatedly or continuously while the garment is worn by the human to monitor the cardiac condition of the human and quickly and accurately detect adverse cardiac conditions in a variety of environments and circumstances, which may enhance safety of the human.

Acceleration measurements may be received 410 from one or more accelerometers of a garment worn by a human. For example, acceleration measurements may be received 410 via conductors that connect one or more motion sensor modules (e.g., the motion sensor module 150), which include an accelerometer, to a processing apparatus (e.g., the processing apparatus 310). For example, acceleration measurements may be received 410 via wireless communications (e.g., using Bluetooth, ZigBee, or WiFi protocols) from one or more motion sensor modules (e.g., the motion sensor module 150), which include an accelerometer, to a processing apparatus (e.g., the processing apparatus 310 or the processing apparatus 340). For example, acceleration measurements may be received 410 by a processing apparatus (e.g., the processing apparatus 370) via network communications (e.g., using IPv4 or IPv6 protocols) through a network interface (e.g., the network interface 376). The received 410 acceleration measurements may be raw measurements or they may be partially processed measurements (e.g., measurements that have been filtered to suppress noise components in a signal).

Electrocardiogram measurements may be received 420 from electrodes of a garment worn by a human. For example, electrocardiogram measurements may be received 420 via conductors that connect electrodes (e.g., the electrodes 130, 132, 134, 136, 138, 140, 142, and/or 144) to a processing apparatus (e.g., the processing apparatus 310). For example, electrocardiogram measurements may be received 420 via wireless communications (e.g., using Bluetooth, ZigBee, or WiFi protocols) from one or more electrocardiogram sensor modules (e.g., the electrocardiogram sensor module 120) to a processing apparatus (e.g., the processing apparatus 310 or the processing apparatus 340). For example, electrocardiogram measurements may be received 420 by a processing apparatus (e.g., the processing apparatus 370) via network communications (e.g., using IPv4 or IPv6 protocols) through a network interface (e.g., the network interface 376). The received 420 electrocardiogram measurements may be raw measurements or they may be partially processed measurements (e.g., measurements that have been filtered to suppress noise components in a signal).

A cardiac condition of the human is determined 430 based on the acceleration measurements and/or the electrocardiogram measurements. In some implementations, a cardiac condition may be determined 430 based on the acceleration measurements, the electrocardiogram measurements, and a machine learning model that has been previously determined based on training data. For example, the techniques 550, 600, and/or 700 (described in relation to FIGS. 5B, 6, and 7) may be used to determine 430 a cardiac condition. For example, one or more features may be determined based on the acceleration measurements and/or the electrocardiogram measurements and the one or more features may be processed with the machine learning model to classify a current cardiac condition. For example, a feature may be determined based on an estimate of an entropy of a normalized power spectral density of a sequence of the acceleration measurements. For example, a feature may be determined based on an estimate of a power spectral density within a frequency band for a sequence of the acceleration measurements. For example, a feature may be determined based on an estimate of an entropy of a normalized power spectral density of a sequence of the electrocardiogram measurements. For example, a feature may be determined based on an estimate of a power spectral density within a frequency band for a sequence of the electrocardiogram measurements. In some implementations, determining 430 a cardiac condition may include determining a pasture pattern (e.g., sitting, standing, walking, running, lying, or fallen) for the human based on the acceleration measurements. The cardiac condition may be determined 430 based in part on the posture pattern. For example, a cardiac condition may be determined by a processing apparatus (e.g., the processing apparatuses 310, 340, and 370).

If (at operation 435) a determined cardiac condition is an adverse cardiac condition (e.g., supraventricular tachycardia or ventricular fibrillation) an alert message that indicates the determined cardiac condition may be displayed and/or transmitted 440. An alert message may also include identifying information about the human wearing the garment. In some implementations, biometric identification is performed based on electrocardiogram measurements from the garment to confirm the identity of the human wearing the garment. For example, an alert message may include information about the confirmed identity of the human. In some implementations, the alert message may include current location information for the human wearing the garment. For example, an alert message may include location information based on output of a global positioning system receiver, which may be include in the garment (e.g., the garment 210) or in a personal computing device that is in communication with the garment (e.g., the personal computing device 220). In some implementations, an alert message may be displayed 440 in a user interface (e.g., the user interface 320 or 350) of the garment or a personal computing device. In some implementations, an alert message may be transmitted 440 to a registered health care provider (e.g., to the health care provider device 250), to a registered device of a contact (e.g., the contact device 252), to a personal computing device (e.g., the personal computing device 220), and/or to the garment (e.g., the garment 210) worn by the human. In some implementations, an alert message may be transmitted via a network interface (e.g., the network interface 346 or the network interface 376). In some implementations electrocardiogram measurements may be sent along with an alert message to a cardiologist (e.g., a cardiologist using the health care provider device 250) who can provide certified medical diagnosis based on the electrocardiogram signals.

If (at operation 435) the determined cardiac condition is not problematic, the monitoring of the human's cardiac condition based on the acceleration measurements and the electrocardiogram measurements being received may continue.

Certain cardiac conditions, such as ventricular fibrillation, may justify immediate intervention to improve a human's chance of survival. In some implementations, a garment may include a defibrillator that enables quick intervention to attempt to save the human from serious harm or death. If (at operation 445) the determined cardiac condition is associated with a need for defibrillation, then a defibrillator may be activated 450 in response to the cardiac condition. For example, the defibrillator may be activated 450 by transmitting a control signal to the garment, where the garment includes an integrated defibrillator. In some implementations, timely defibrillation is applied to the human wearing the garment responsive to detection of an adverse cardiac condition (e.g., ventricular fibrillation) as potentially lifesaving first aid when an emergency occurs.

In some implementations, technique 400 may be applied to monitor cardiac condition continuously over a long period of time while a garment is being worn. For example, continuous monitoring may increase the chances of detecting unexpected emergency cardiac conditions, such as ventricular fibrillation. In some implementations, technique 400 may be applied to monitor cardiac condition episodically within a short time frame in response to a triggering event (e.g., a measurement command issued through a user interface of a garment or a personal computing device), which may conserve power and/or memory.

Figure 5A:
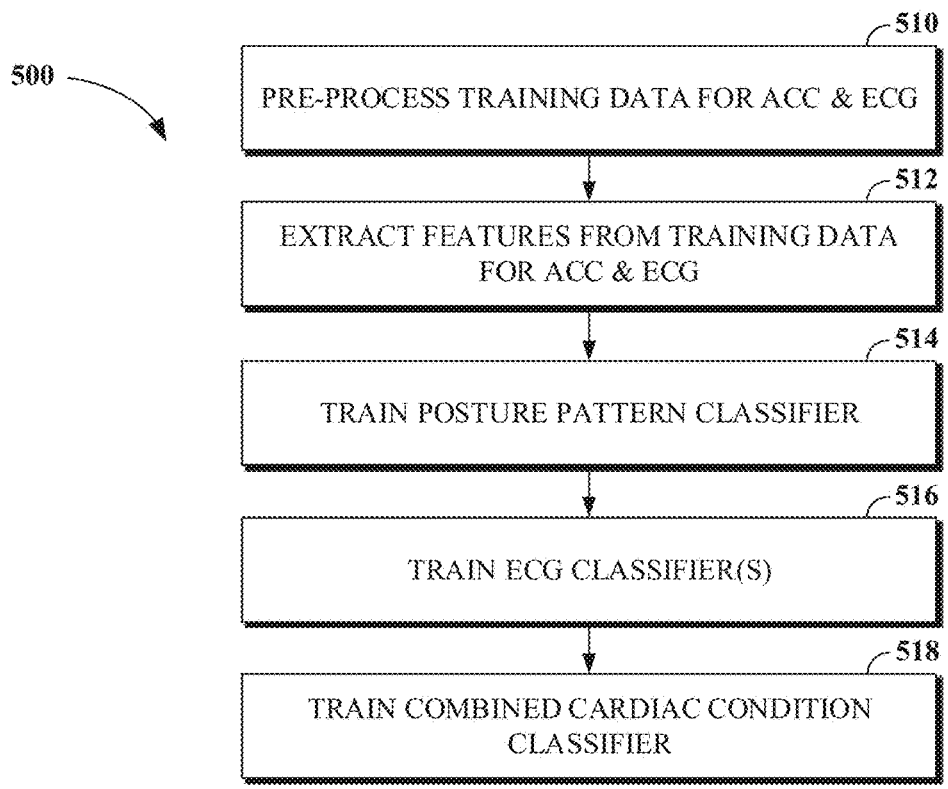
FIG. 5A is a flowchart of an example technique for training machine learning models based on acceleration and/or electrocardiogram training data.

FIG. 5A is a flowchart of an example technique 500 for training machine learning models based on acceleration and/or electrocardiogram training data. For example, technique 500 may be applied off-line to training data, which may include associated labels, acquired over a considerable period of time from one or more humans in order to configure and/or calibrate a system for cardiac condition detection. One or more machine learning models trained using technique 500 may be applied (e.g., using technique 550 of FIG. 5B) to determine a cardiac condition. Technique 500 may include pre-processing 510 acceleration measurements and/or electrocardiogram measurements included in training data, extracting 512 features based on the acceleration measurements and/or electrocardiogram measurement included in training data, training 514 a posture pattern classifier, training 516 an electrocardiogram classifier, and training 518 a combined cardiac condition classifier. For example, technique 500 may be implemented by a processing apparatus (e.g., the processing apparatuses 310, 340, and 370).

Acceleration measurements from a corpus of training data may be pre-processed 510 to prepare the measurements for further processing. In some implementations, pre-processing 510 the acceleration measurements may include correcting signal baseline drift and/or suppression of other high-frequency noise due to possible motion artifacts. For example, pre-processing 510 the acceleration measurements may include filtering a sequence of acceleration measurements (e.g., using a moving average over a sliding time window, using an exponential moving average, using Wiener Filtering, and/or using other forms of adaptive filtering).

Electrocardiogram measurements from a corpus of training data may be pre-processed 510 to prepare the measurements for further processing. In some implementations, pre-processing 510 the electrocardiogram measurements may include suppression of noise in the measurements (e.g., due to power line interference or possible motion artifacts). For example, pre-processing 510 the electrocardiogram measurements may include filtering a sequence of electrocardiogram measurements (e.g., using a moving average over a sliding time window, using an exponential moving average, using Wiener Filtering, and/or using other forms of adaptive filtering).

Features may be extracted 512 based on acceleration measurements (e.g., pre-processed acceleration measurements) from the training data. For example, a feature extracted 512 may be determined based on an estimate of an entropy of a normalized power spectral density of a sequence of the acceleration measurements. For example, a feature extracted 512 may be determined based on an estimate of a power spectral density within a frequency band for a sequence of the acceleration measurements. Other features extracted 512 may include, for example, a mean, a standard deviation, a zero-crossing rate, a signal magnitude area, skewness/kurtosis statistics, or correlation coefficients for a sequence of acceleration measurements for an axis of an accelerometer fastened to a position on the human (e.g., on the human's chest, lower back, wrist, waist, hip, thigh, or foot) over a window of time.

Features may be extracted 512 based on electrocardiogram measurements (e.g., pre-processed electrocardiogram measurements) from the training data. For example, a feature extracted 512 may be determined based on an estimate of an entropy of a normalized power spectral density of a sequence of the electrocardiogram measurements. For example, a feature extracted 512 may be determined based on an estimate of a power spectral density within a frequency band for a sequence of the electrocardiogram measurements. Other features extracted 512 may include, for example, PQRST complex fiducial points, R peak to R peak related features (e.g., heart rate), fast Fourier transform (FFT) based features, wavelet transform based features, or alternating current discrete cosine transform (AC-DCT) based features, for a sequence of electrocardiogram measurements for a lead (e.g., a precordial lead, lead I, lead II, lead III, lead aVR, lead aVL, or lead aVF) over a window of time.

A posture pattern classifier may be trained 514 based on acceleration measurements from the training data. For example, the posture pattern classifier may be trained 516 based on features extracted 512 from the acceleration measurements from the training data. The acceleration measurements from the training data may be associated with labels of the posture pattern exhibited by the human at the time the acceleration measurements were detected and/or recorded. For example, the posture pattern classifier may be implemented as a variety of types of machine learning models including a support vector machine (SVM), a Bayesian Model, a decision tree, etc. Appropriate supervised learning techniques may be applied to train 514 the posture pattern classifier based on the training data with associated posture pattern labels.

An electrocardiogram classifier may be trained 516 based on electrocardiogram measurements from the training data. For example, the electrocardiogram classifier may be trained 516 based on features extracted 512 from the electrocardiogram measurements from the training data. The electrocardiogram measurements from the training data may be associated with labels of a cardiac condition experienced by the human at the time the electrocardiogram measurements were detected and/or recorded. For example, the electrocardiogram classifier may be implemented as a variety of types of machine learning models including a support vector machine (SVM), a Bayesian model, a decision tree, etc. Appropriate supervised learning techniques may be applied to train 516 the electrocardiogram classifier based on the training data with associated cardiac condition labels.

A combined cardiac condition classifier may be trained 518 based on electrocardiogram measurements and acceleration measurements from the training data. For example, the combined cardiac condition classifier may be trained 518 based on features extracted 512 from the electrocardiogram measurements and the acceleration measurements from the training data. In some implementations, the combined cardiac condition classifier may take the output of the posture pattern classifier as an input feature. In some implementations, the combined cardiac condition classifier may take the output of the electrocardiogram classifier as an input feature. In some implementations, the combined cardiac condition classifier may take features extracted 512 from the electrocardiogram measurements and the acceleration measurements as input features. For example, the combined cardiac condition classifier may be implemented as a variety of types of machine learning models including a support vector machine (SVM), a Bayesian model, a decision tree, etc. Appropriate supervised learning techniques may be applied to train 518 the combined cardiac condition classifier based on the training data with associated cardiac condition labels.

In some implementations, the corpus of training data may include acceleration measurements and/or electrocardiogram measurements that have been gathered from the human using the garment. For example, personalized adaptation to aspects of an individual human's activity patterns and/or cardiac response may be accomplished by analyzing training data from the same human that will be monitored using the garment. For example, a user may be prompted through the user interface of a personal computing device (the user interface 350) to select training labels for their activity and posture while collecting training data with the garment. In some implementations, the corpus of training data may include acceleration measurements and/or electrocardiogram measurements that have been gathered from many different humans using similar garments or a variety of different measurement devices, which may be operated in controlled environments to generate training data with labels for activity/posture and/or for cardiac condition.

Figure 5B:
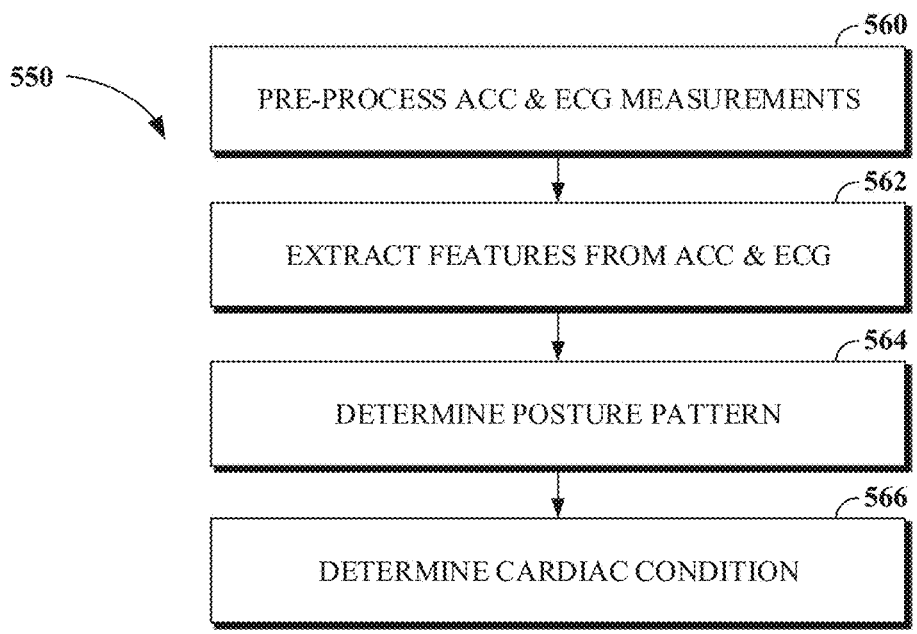
FIG. 5B is a flowchart of an example technique for determining a posture pattern and a cardiac condition based on machine learning models.

FIG. 5B is a flowchart of an example technique 550 for determining a posture pattern and a cardiac condition based on machine learning models. Technique 550 may utilize one or more machine learning models trained using training data (e.g., using technique 500 of FIG. 5A). Technique 550 may include pre-processing 560 acceleration measurements and/or electrocardiogram measurements from a garment worn by a human, extracting 562 features based on the acceleration measurements and/or electrocardiogram measurements, determining 564 a posture pattern of the human wearing the garment, and determining 566 a cardiac condition of the human wearing the garment. For example, technique 550 may be implemented by a processing apparatus (e.g., the processing apparatuses 310, 340, and 370).

Acceleration measurements from one or more accelerometers of a garment worn by a human may be pre-processed 560 to prepare the measurements for further processing. In some implementations, pre-processing 560 the acceleration measurements may include correcting signal baseline drift and/or suppression of other high-frequency noise due to possible motion artifacts. For example, pre-processing 560 the acceleration measurements may include filtering a sequence of acceleration measurements (e.g., using a moving average over a sliding time window, using an exponential moving average, using Wiener Filtering, and/or using other forms of adaptive filtering).

Electrocardiogram measurements from electrodes of a garment worn by a human may be pre-processed 560 to prepare the measurements for further processing. In some implementations, pre-processing 560 the electrocardiogram measurements may include suppression of noise in the measurements (e.g., due to power line interference or to possible motion artifacts). For example, pre-processing 560 the electrocardiogram measurements may include filtering a sequence of electrocardiogram measurements (e.g., using a moving average over a sliding time window, using an exponential moving average, using Wiener Filtering, and/or using other forms of adaptive filtering).

Features may be extracted 562 based on acceleration measurements (e.g., pre-processed acceleration measurements) from one or more accelerometers of a garment worn by a human. For example, a feature extracted 562 may be determined based on an estimate of an entropy of a normalized power spectral density of a sequence of the acceleration measurements. For example, a feature extracted 562 may be determined based on an estimate of a power spectral density within a frequency band for a sequence of the acceleration measurements. Other features extracted 562 may include, for example, a mean, a standard deviation, a zero-crossing rate, a signal magnitude area, skewness/kurtosis statistics, or correlation coefficients for a sequence of acceleration measurements for an axis of an accelerometer fastened to a position on the human (e.g., on the human's chest, lower back, wrist, waist, hip, thigh, or foot) over a window of time.

Features may be extracted 562 based on electrocardiogram measurements (e.g., pre-processed electrocardiogram measurements) from electrodes of a garment worn by a human. For example, a feature extracted 562 may be determined based on an estimate of an entropy of a normalized power spectral density of a sequence of the electrocardiogram measurements. For example, a feature extracted 562 may be determined based on an estimate of a power spectral density within a frequency band for a sequence of the electrocardiogram measurements. Other features extracted 562 may include, for example, PQRST complex fiducial points, R peak to R peak related features (e.g., heart rate), fast Fourier transform (FFT) based features, wavelet transform based features, or alternating current discrete cosine transform (AC-DCT) based features, for a sequence of electrocardiogram measurements for a lead (e.g., a precordial lead, lead I, lead II, lead III, lead aVR, lead aVL, or lead aVF) over a window of time.

A posture pattern of the human may be determined 564 based on the acceleration measurements. For example, a posture pattern may be determined 564 by inputting features extracted 562 from the acceleration measurements from a garment worn by the human to a machine learning model (e.g., a posture pattern classifier described in relation to FIG. 5A) that has been determined based on training data. For example, the determined 564 posture pattern may correspond to fallen condition of the human (e.g., the human has collapsed suddenly). For example, the determined 564 posture pattern may be sitting, standing, walking, running, lying, or fallen. In some implementations, the posture pattern may be determined 564 based in part on a feature that is based on an estimate of an entropy of a normalized power spectral density of a sequence of the acceleration measurements. In some implementations, the posture pattern may be determined 564 based in part on a feature that is based on an estimate of a power spectral density within a frequency band for a sequence of the acceleration measurements.

A cardiac condition of a human may be determined 566 based on the acceleration measurements, the electrocardiogram measurements, and a machine learning model previously determined based on training data. For example, a cardiac condition may be determined 566 by inputting features extracted 562 from the electrocardiogram measurements and/or the acceleration measurements from a garment worn by the human to a machine learning model (e.g., a combined cardiac condition classifier and/or an electrocardiogram classifier described in relation to FIG. 5A) that has been determined based on training data. In some implementations, the cardiac condition may be determined 566 using a combined cardiac condition classifier (as described in relation to FIG. 5A) configured to take the determined 564 posture pattern as an input feature. In some implementations, the cardiac condition may be determined 566 using a combined cardiac condition classifier (as described in relation to FIG. 5A) configured to take the output of the electrocardiogram classifier (as described in relation to FIG. 5A) as an input feature. In some implementations, the cardiac condition may be determined 566 using a combined cardiac condition classifier (as described in relation to FIG. 5A) configured to take features extracted 562 from the electrocardiogram measurements and the acceleration measurements as input features. For example, technique 600 of FIG. 6 may be used to determine 566 whether the human wearing the garment is experiencing a ventricular fibrillation condition. For example, technique 700 of FIG. 7 may be used to determine whether the human wearing the garment is experiencing a supraventricular tachycardia condition. In some implementations, the cardiac condition may be determined 566 based in part on a feature that is based on an estimate of an entropy of a normalized power spectral density of a sequence of the acceleration measurements. In some implementations, the cardiac condition may be determined 566 based in part on a feature that is based on an estimate of a power spectral density within a frequency band for a sequence of the acceleration measurements. In some implementations, the cardiac condition may be determined 566 based in part on a feature that is based on an estimate of an entropy of a normalized power spectral density of a sequence of the electrocardiogram measurements. In some implementations, the cardiac condition may be determined 566 based in part on a feature that is based on an estimate of a power spectral density within a frequency band for a sequence of the electrocardiogram measurements. In some implementations, the cardiac condition may be determined 566 based in part on a posture pattern that has been determined 564. In some implementations, the cardiac condition may be determined 566 based in part on a feature that is based on an estimate of a fiducial point of a QRS complex in a sequence of the electrocardiogram measurements.

Figure 6:
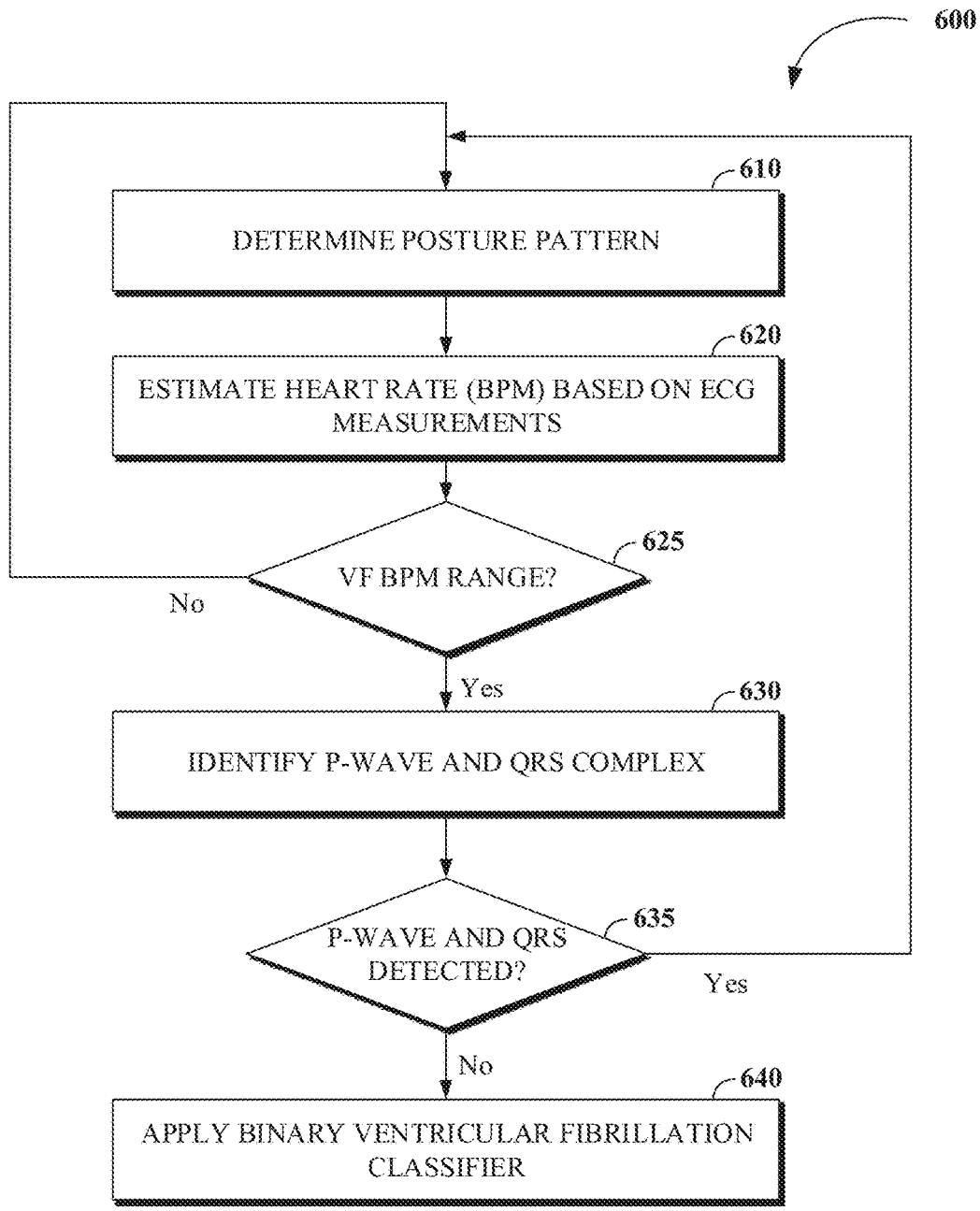
FIG. 6 is a flowchart of an example technique for detecting a ventricular fibrillation condition.

FIG. 6 is a flowchart of an example technique 600 for detecting a ventricular fibrillation condition. For example, technique 600 may detect a ventricular fibrillation condition based in part on estimating a heart rate that is either far above rate expected for the current posture pattern of the human or even unreadable due to an unrecognizable morphology of an electrocardiogram signal (e.g., R peaks cannot be reliably identified). For example, technique 600 may be implemented by a processing apparatus (e.g., the processing apparatuses 310, 340, and 370).

A posture pattern (e.g., sitting, walking, running, fallen) may be determined 610 based on acceleration measurements from one or more accelerometers of a garment worn by a human. For example, the posture pattern may be determined 610 as described in relation to operation 564 of FIG. 5B. A heart rate (e.g., in beats-per-minute) may be estimated 620 based on electrocardiogram measurements from electrodes of the garment. For example, a number of R peaks detected within a time window of known duration for one or more leads (e.g., a precordial lead or lead I) from a sequence of electrocardiogram measurements may be counted to estimate the heart rate of the human. For example, a heart rate may be estimated 620 based in part on determining an autocorrelation function for a sequence of the electrocardiogram measurements at various lags.

The estimated 620 heart rate may then be compared (at operation 625) to a range associated with the current posture pattern determined 610 for the human. For example, a heart rate while sitting may be expected to be in a range between 60 and 100 BPM (beats-per-minute). An estimated 620 heart rate substantially above the expected range may be indicative of a possible ventricular fibrillation condition. For example, if (at operation 625) the estimated 620 heart rate is, while the human is determined 610 to be is a sitting posture pattern, in the range between 150 and 500 BPM, then analysis to determine whether a ventricular fibrillation condition is occurring will proceed, otherwise the system may continue monitoring unless and until the heart rate is estimated to be in this range. The expected range of heart rates may vary with the posture pattern the ventricular fibrillation detection range of heart rates may be adjusted accordingly. In implementations where training data for the individual human wearing the garment has been collected, the applicable heart rate ranges for the various posture patterns may be narrowed and tailored to the individual human.

If (at operation 625) the estimated 620 heart rate is within the range for ventricular fibrillation associated with the human's determined 610 posture pattern, then analysis continues by attempting to identify 630 a P-wave and QRS complex within a time window for one or more leads (e.g., a precordial lead and/or lead I) from a sequence of electrocardiogram measurements. For example, the Pan-Tompkins algorithm may be used to identify 630 a QRS complex and P-Wave. For example, a wavelet transform (e.g., using a symlet 4 wavelet) may be used help identify 630 the QRS complex. The P-wave and QRS complex are discussed more in relation to FIG. 10.

If (at operation 635) both a P-wave and a QRS complex have been successfully identified 630, then it is most likely not an occurrence of ventricular fibrillation and the monitoring process can continue. For example, of a detectable P-wave and QRS complex at elevated heart rates may be associated with a potential supraventricular tachycardia condition and analysis to detect a potential supraventricular tachycardia condition (e.g., using technique 700 to check for supraventricular tachycardia) may be applied.

If (at operation 635) either a P-wave and a QRS complex have not been successfully identified 630, then a binary ventricular fibrillation classifier may be applied 640 to features that are based in the electrocardiogram measurements and/or the acceleration measurements from the garment worn by the human. For example, an electrocardiogram classifier and/or a combined cardiac condition classifier that has been determined based on a corpus of training data (e.g., as described in relation to FIG. 5A) may be applied 640. The binary ventricular fibrillation classifier may determine whether a ventricular fibrillation condition is occurring.

Figure 7:
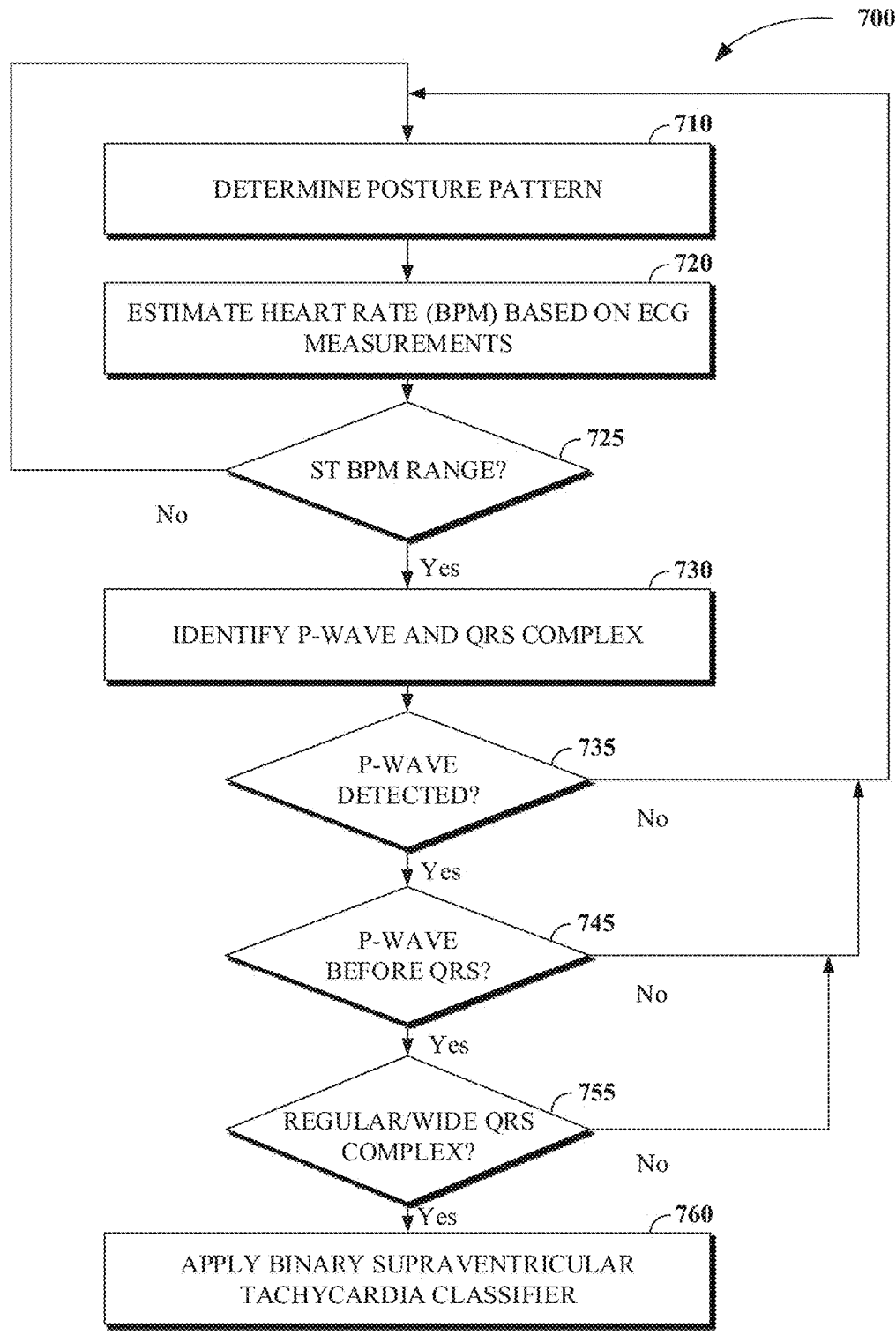
FIG. 7 is a flowchart of an example technique for detecting a supraventricular tachycardia condition.

FIG. 7 is a flowchart of an example technique 700 for detecting a supraventricular tachycardia condition. For example, technique 700 may detect a supraventricular tachycardia condition based in part on estimating a heart rate that is in a range associated with the disorder and outside an expected range for the current posture pattern of the human being monitored. For example, technique 700 may be implemented by a processing apparatus (e.g., the processing apparatuses 310, 340, and 370).

A posture pattern (e.g., sitting, walking, running, fallen) may be determined 710 based on acceleration measurements from one or more accelerometers of a garment worn by a human. For example, the posture pattern may be determined 710 as described in relation to operation 564 of FIG. 5B. A heart rate (e.g., in beats-per-minute) may be estimated 720 based on electrocardiogram measurements from electrodes of the garment. For example, a number of R peaks detected within a time window of known duration for one or more leads (e.g., a precordial lead or lead I) from a sequence of electrocardiogram measurements may be counted to estimate the heart rate of the human. For example, a heart rate may be estimated 720 based in part on determining an autocorrelation function for a sequence of the electrocardiogram measurements at various lags.

The estimated 720 heart rate may then be compared (at operation 725) to a range associated with the current posture pattern determined 710 for the human. For example, a human experiencing a supraventricular tachycardia condition while sitting may be expected to manifest a heart rate in a range between 110 and 264 BPM. An estimated 720 heart rate in this range and a determination 710 of a sitting posture pattern may be indicative of a possible supraventricular tachycardia condition.

For example, if (at operation 725) the estimated 720 heart rate is, while the human is determined 710 to be is a sitting posture pattern, in the range between 110 and 264 BPM, then analysis to determine whether a supraventricular tachycardia condition is occurring will proceed, otherwise the system may continue monitoring unless and until the heart rate is estimated to be in this range. The expected range of heart rates may vary with the posture pattern and the supraventricular tachycardia detection range of heart rates may be adjusted accordingly. In implementations where training data for the individual human wearing the garment has been collected, the applicable heart rate ranges for the various posture patterns may be narrowed and tailored to the individual human. In some implementations, supraventricular tachycardia detection may be enabled when the human is determined 710 to be in a posture pattern associated with rest (e.g., sitting, standing, or lying) and the system may wait until wait until a restful posture pattern is detected to evaluate whether a supraventricular tachycardia condition is occurring.

If (at operation 725) the estimated 720 heart rate is within the range for supraventricular tachycardia associated with the human's determined 610 posture pattern, then analysis proceeds by attempting to identify 730 a P-wave and QRS complex within a time window for one or more leads (e.g., a precordial lead and/or lead I) from a sequence of electrocardiogram measurements. For example, the Pan-Tompkins algorithm may be used to identify 730 a QRS complex and P-Wave. For example, a wavelet transform (e.g., using a symlet 4 wavelet) may be used help identify 730 the QRS complex. The P-wave and QRS complex are discussed more in relation to FIG. 10.

If (at operation 735) a P-wave has been identified 730, then the supraventricular tachycardia analysis proceeds. Otherwise, the cardiac condition is probably not supraventricular tachycardia and monitoring may continue. For example, a lack of a detectable P-wave may be associated with a potential AVNRT (atrioventricular nodal reentrant tachycardia) condition or an atrial fibrillation condition and analysis to detect a potential AVNRT condition and/or a potential atrial fibrillation condition may be applied.

If (at operation 745) an identified 730 P-wave is before a corresponding identified 730 QRS complex, then the supraventricular tachycardia analysis proceeds. Otherwise, the cardiac condition is probably not supraventricular tachycardia and monitoring may continue. For example, a lagging P-wave may be associated with a potential uncommon AVNRT condition and analysis to detect a potential uncommon AVNRT condition may be applied.

If (at operation 755) an identified 730 QRS complex is or regular width or wider, then the supraventricular tachycardia analysis proceeds. Otherwise, the cardiac condition is probably not supraventricular tachycardia and monitoring may continue. For example, a narrow QRS complex may be associated with a potential AVNRT condition and analysis to detect a potential AVNRT condition may be applied.

Where all the tests at operations 725, 735, 745, and 755 are met, technique 700 may proceed by applying 760 a binary supraventricular tachycardia classifier may be applied 640 to features that are based on the electrocardiogram measurements and/or the acceleration measurements from the garment worn by the human. For example, an electrocardiogram classifier and/or a combined cardiac condition classifier that has been determined based on a corpus of training data (e.g., as described in relation to FIG. 5A) may be applied 760. The binary supraventricular tachycardia classifier may determine whether a supraventricular tachycardia condition is occurring.

Figure 8A:
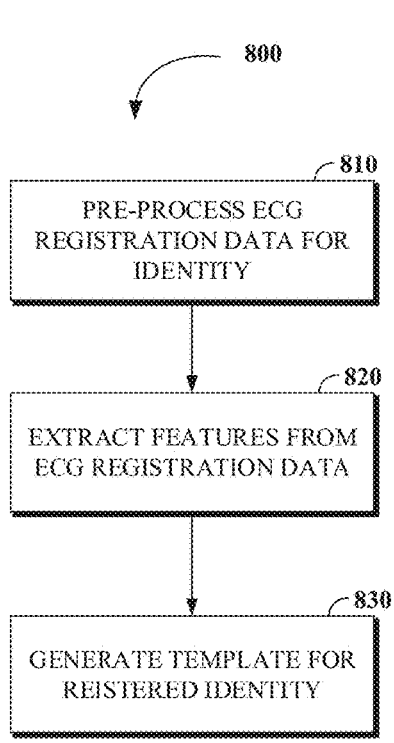
FIG. 8A is a flowchart of an example technique for determining a template for registered identity that is based on electrocardiogram registration data.

FIG. 8A is a flowchart of an example technique 800 for determining a template for a registered identity that is based on electrocardiogram registration data. Technique 800 may include pre-processing 810 electrocardiogram measurements collected as registration data for an identity, extracting 820 features from the electrocardiogram measurements in the registration data, and generating 830 a template for the registered identity based on the features. For example, technique 800 may be implemented by a processing apparatus (e.g., the processing apparatuses 310, 340, and 370).

Electrocardiogram measurements from identity registration data may be pre-processed 810 to prepare the measurements for further processing. For example, registration data for an identity may be collected using a garment (e.g., the garment 100 or the garment 210) operating in an identity registration mode. In some implementations, pre-processing 810 the electrocardiogram measurements may include suppression of noise in the measurements (e.g., due to power line interference or possible motion artifacts). For example, pre-processing 810 the electrocardiogram measurements may include filtering a sequence of electrocardiogram measurements (e.g., using a moving average over a sliding time window, using an exponential moving average, using Wiener Filtering, and/or using other forms of adaptive filtering).

Features may be extracted 820 from the pre-processed electrocardiogram measurements from the registration data. For example, a feature extracted 820 may be determined based on an estimate of an entropy of a normalized power spectral density of a sequence of the electrocardiogram measurements. For example, a feature extracted 820 may be determined based on an estimate of a power spectral density within a frequency band for a sequence of the electrocardiogram measurements. Other features extracted 820 may include, for example, PQRST complex fiducial points, fast Fourier transform (FFT) based features, wavelet transform based features, or alternating current discrete cosine transform (AC-DCT) based features, for a sequence of electrocardiogram measurements for a lead (e.g., a precordial lead, lead I, lead II, lead III, lead aVR, lead aVL, or lead aVF) over a window of time. As an optional step, dimension reduction techniques, such as PCA, can be applied to the feature data sets to reduce dimensionality.

A template may be generated 830 for the registered identity based on the extracted 820 features. For example, the template may include an array of the extracted 820 features. For example, the template may be stored and associated with the registered identity.

Figure 8B:
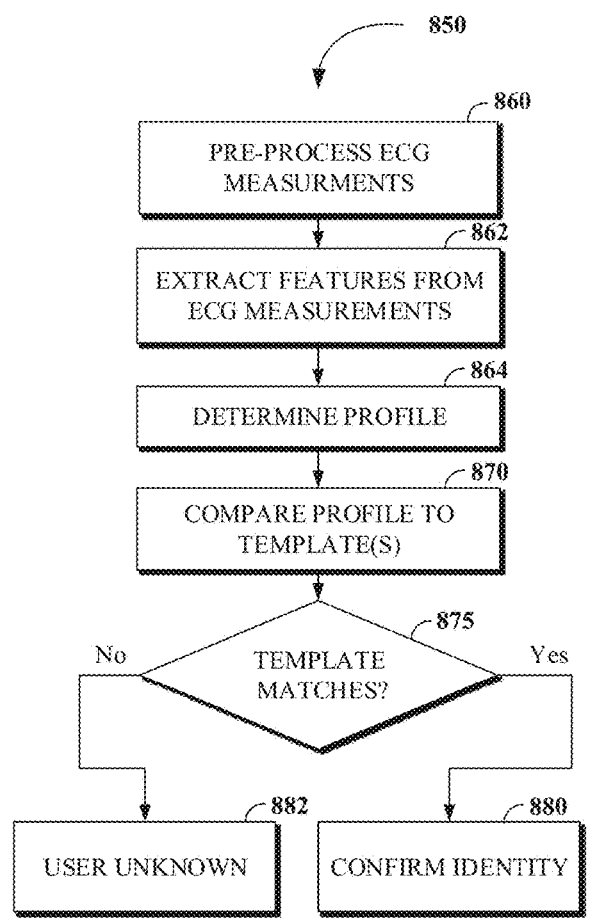
FIG. 8B is a flowchart of an example technique for confirming the identity of a user by comparing a profile based on electrocardiogram data to a template associated with an identity.

FIG. 8B is a flowchart of an example technique 850 for confirming the identity of a user by comparing a profile based on electrocardiogram data to a template associated with an identity. Technique 850 may include pre-processing 860 electrocardiogram measurements from electrodes in a garment worn by a human, extracting 862 features from the pre-processed electrocardiogram measurements, determining 864 a profile for the human based on the features, comparing 870 the profile to one or more templates associated with a registered identity, and confirming 880 the identity of the human response to a match of the profile with a template. For example, technique 850 may be implemented by a processing apparatus (e.g., the processing apparatuses 310, 340, and 370).

Electrocardiogram measurements from electrodes in a garment worn by the human may be pre-processed 860 to prepare the measurements for further processing. In some implementations, pre-processing 860 the electrocardiogram measurements may include suppression of noise in the measurements (e.g., due to power line interference or possible motion artifacts). For example, pre-processing 860 the electrocardiogram measurements may include filtering a sequence of electrocardiogram measurements (e.g., using a moving average over a sliding time window, using an exponential moving average, using Wiener Filtering, and/or using other forms of adaptive filtering).

Features may be extracted 862 from the pre-processed electrocardiogram measurements from the electrodes of the garment. For example, a feature extracted 862 may be determined based on an estimate of an entropy of a normalized power spectral density of a sequence of the electrocardiogram measurements. For example, a feature extracted 862 may be determined based on an estimate of a power spectral density within a frequency band for a sequence of the electrocardiogram measurements. Other features extracted 862 may include, for example, PQRST complex fiducial points, fast Fourier transform (FFT) based features, wavelet transform based features, or alternating current discrete cosine transform (AC-DCT) based features, for a sequence of electrocardiogram measurements for a lead (e.g., a precordial lead, lead I, lead II, lead III, lead aVR, lead aVL, or lead aVF) over a window of time. As an optional step, dimension reduction techniques, such as PCA, can be applied to the feature data sets to reduce dimensionality.

A profile may be determined 864 for human wearing the garment based on the extracted 862 features. For example, the profile may include an array of the extracted 862 features.

The determined 864 profile may be compared 870 to one or more registered templates that are, respectively, associated with an identity. In some implementations, the profile is compared 870 to one or more templates by passing features of the profile to a machine learning based classifier (e.g., based on linear discriminant analysis) that has been trained to match profiles to a set of one or more templates. For example, a decision tree classifier may be used to compare 870 the profile to a registered template. In some implementations, the profile is compared 870 to a template by determining a distance metric between the profile (as a vector of features) and the template (as vector of features). For example, a Euclidean distance between the profile and the template may be calculated and compared to a threshold that has been determined based on analysis of a large corpus of registration templates. If the distance metric is below the threshold, the profile may be determined to match the template, and not match otherwise.

If (at operation 875), based on the comparison 870, the profile is determined to match a registered template, then the identity of the human wearing the garment may be confirmed 880 to be the identity associated with the registered template. For example, information about the confirmed identity of the human may be displayed or transmitted along with an alert message that indicates the determined cardiac condition (e.g., as described in relation to operation 440 of FIG. 4).

If (at operation 875), based on the comparison 870, the profile is determined not to match a registered template, then a user unknown result may be returned 882. For example, message indicating the human wearing the garment is not recognized may be displayed or transmitted.

Figure 9A:
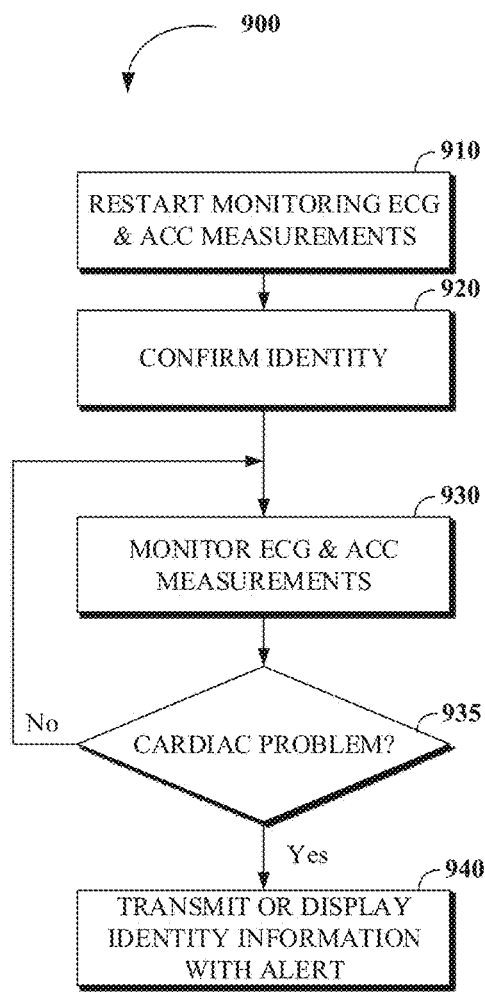
FIG. 9A is a flowchart of an example technique for transmitting confirmed identity information with an alert regarding a cardiac condition.

FIG. 9A is a flowchart of an example technique 900 for transmitting confirmed identity information with an alert regarding a cardiac condition. Technique 900 may include restarting 910 monitoring of electrocardiogram measurements and/or acceleration measurements from a garment worn by a human; confirming 920 the identity of the human; continuing to monitor 930 the electrocardiogram measurements and/or acceleration measurements from the garment worn by the human; and, when (at operation 935) a cardiac condition problem is detected, transmitting or displaying 940 the confirmed identity information along with a cardiac condition alert message. For example, technique 900 may be implemented by a processing apparatus (e.g., the processing apparatuses 310, 340, and 370).

Monitoring of the human wearing the garment may be restarted 910, for example, when the garment is put on by the human and/or activated through a user interface (e.g., the user interface 320 or the user interface 350). For example, the identity of the human may be confirmed 920 using technique 850. For example, the human wearing the garment may be monitored 930 using technique 400 (described in relation to FIG. 4). For example, information about the confirmed identity of the human may be displayed or transmitted 940 along with an alert message that indicates the determined cardiac condition (e.g., as described in relation to operation 440 of FIG. 4).

Figure 9B:
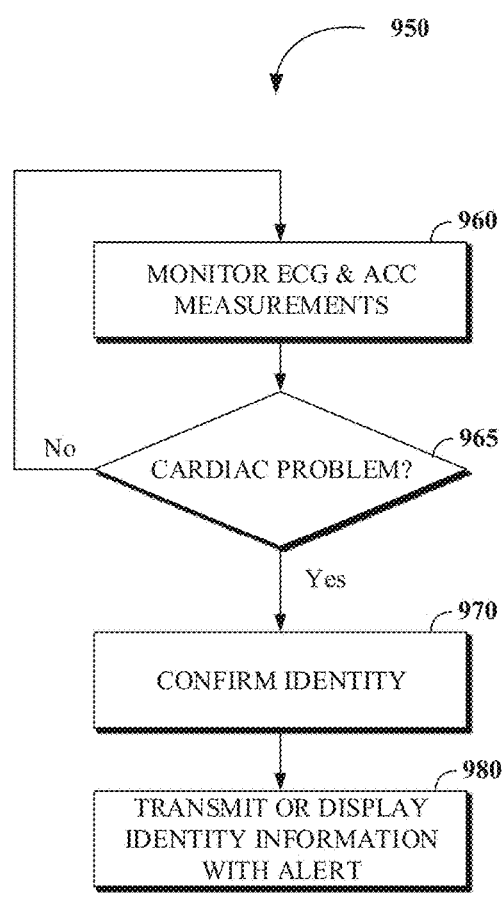
FIG. 9B is a flowchart of an example technique for transmitting confirmed identity information with an alert regarding a cardiac condition.

FIG. 9B is a flowchart of an example technique 950 for transmitting confirmed identity information with an alert regarding a cardiac condition. Technique 950 may include monitoring 960 of electrocardiogram measurements and/or acceleration measurements from a garment worn by a human; when (at operation 965) a cardiac condition problem is detected, confirming 970 the identity of the human; and transmitting or displaying 980 the confirmed identity information along with a cardiac condition alert message. For example, technique 950 may be implemented by a processing apparatus (e.g., the processing apparatuses 310, 340, and 370).

For example, the human wearing the garment may be monitored 960 using technique 400 (described in relation to FIG. 4). For example, the identity of the human may be confirmed 970 using technique 850. For example, information about the confirmed identity of the human may be displayed or transmitted 980 along with an alert message that indicates the determined cardiac condition (e.g., as described in relation to operation 440 of FIG. 4).

Figure 10:
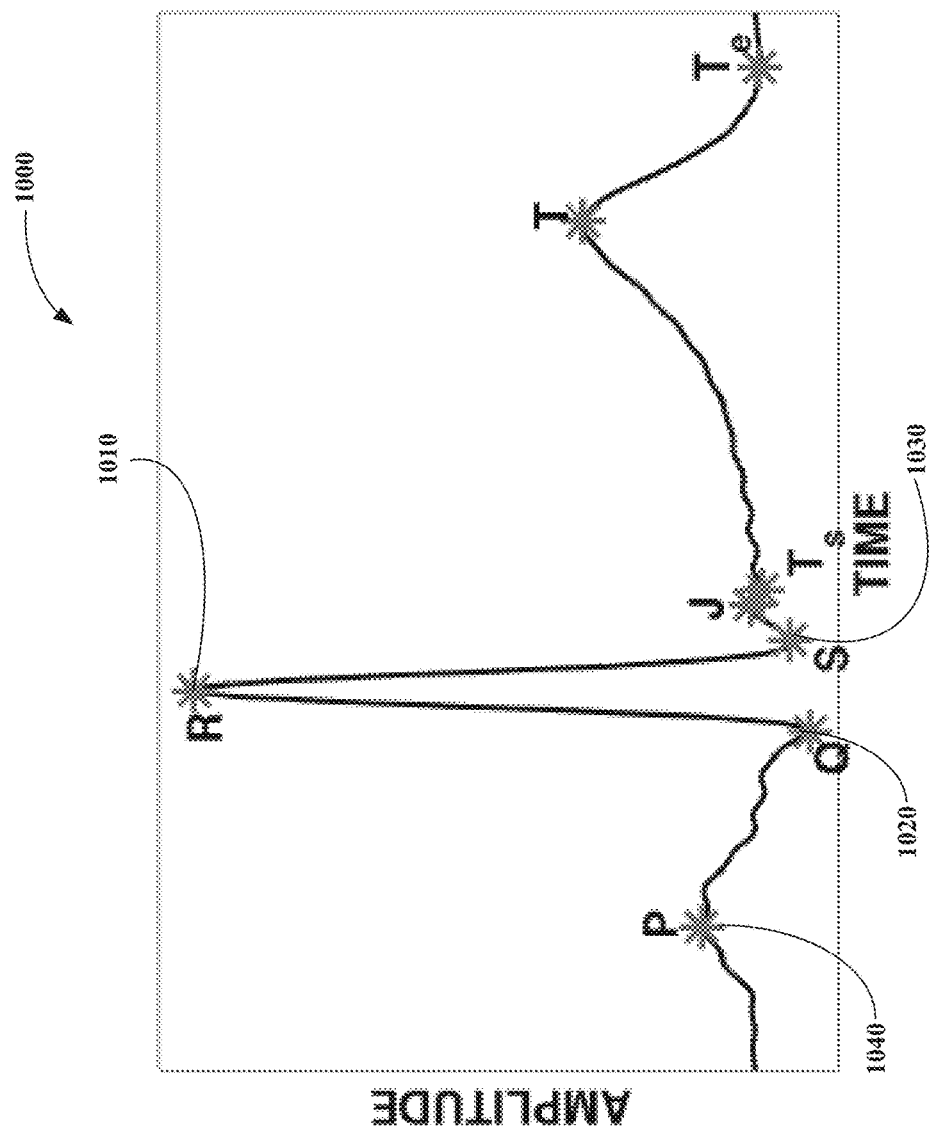
FIG. 10 is an example plot of a portion of an electrocardiogram signal.

FIG. 10 is an example plot 1000 of a portion of an electrocardiogram signal with a number of fiducial points illustrated. For example, plot 1000 may depict is preprocessed electrocardiogram measurements (e.g., resulting from operation 560) for a lead (e.g., a precordial lead) over time interval corresponding to approximately one heart beat. The output curve generally represents voltage over time, but any appropriate measurement unit may be used. A typical electrocardiogram output is a repeating cycle formed of a P-wave 1040 (representing atrial depolarization), a QRS complex (representing ventricular depolarization) and a T-wave (representing ventricular repolarization). A PR segment exists from the end of the P-wave to the beginning of the QRS complex, and an ST segment exists from the end of the QRS complex to the beginning of the T-wave. Other electrical entities may be represented in a sequence of electrocardiogram measurements.

Each of these electrical entities within an electrocardiogram curve is associated with one or more amplitudes (used interchangeably with magnitude herein unless otherwise noted) and one or more time intervals or durations. For example, in the QRS complex, the Q point 1020 and S point 1030 are valleys and R point 1010 is a peak, each associated with a different amplitude. The amplitude of any point within can be either an absolute amplitude (measured relative to the baseline) or a relative amplitude (measured as compared to another amplitude). Using absolute measurements, for example, FIG. 10 shows that valley Q has a Q-wave magnitude, peak R has an R-wave magnitude, and valley S has an S-wave magnitude. The magnitude of the T-wave and the magnitude of the P-wave 1040 are also shown in FIG. 10. An interval or duration may be measured from any point in the repeating cycle to any other point. For example, one fiducial point may be represented by a PR interval from the start of the P-wave 1040 to the start of the QRS complex and a QT interval from the start of the QRS complex to the end of the T-wave.

Using the fiducial based approach, feature extraction in FIG. 10 involves detecting or calculating at least some of the durations/intervals and at least some of the amplitudes/magnitudes within the electrocardiogram curve or waveform. Feature extraction may be achieved using calculations including one or more of a spectral based feature, wavelet, discrete cosine transformation (DCT), power density, Ensemble Empirical Mode Decomposition (EEMD). The features could be the amplitude and duration values themselves, combinations of the amplitude and/or duration values or values derived using the amplitude and/or duration values through, for example, Autocorrelation Coefficient (AC) or a Periodicity Transform (PT). One feature may be, for example, heart rate variability (HRV), which is the variation of beat-to-beat intervals (i.e., the time from R to R per cycle). The features may be reduced or encoded using principal component analysis (PCA), linear discriminant analysis (LDA) and/or independent component analysis (ICA).

While the disclosure has been described in connection with certain embodiments, it is to be understood that the disclosure is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A system, comprising:
   a garment comprising a plurality of electrodes and one or more accelerometers; and
   a processing apparatus that is configured to:
   receive acceleration measurements from the one or more accelerometers;
   receive electrocardiogram measurements from the plurality of electrodes;
   determine a posture pattern of a human based on the acceleration measurements;
   determine a cardiac condition of the human based on the posture pattern and the electrocardiogram measurements by inputting features extracted from the electrocardiogram measurements and the posture pattern to a machine learning model previously determined based on training data; and
   transmit or display an alert message that indicates the determined cardiac condition.

2. The system of claim 1, in which the one or more accelerometers comprise:
   a first accelerometer that is positioned, as a component of the garment, such that the first accelerometer is capable of being fastened to a chest of the human.

3. The system of claim 2, in which the one or more accelerometers comprise:
   a second accelerometer that is positioned, as a component of the garment, such that the second accelerometer is capable of being fastened to a waist of the human.

4. The system of claim 1, in which the processing apparatus is attached to the garment.

5. The system of claim 1, in which the garment comprises:
one or more motion sensor modules that include the one or more accelerometers;
an electrocardiogram sensor module that is connected via conductors to the plurality of electrodes and detects the electrocardiogram measurements from the electrodes; and
conductors that connect the processing apparatus to the electrocardiogram sensor module and to the one or more motion sensor modules.

6. The system of claim 1, in which the processing apparatus is configured to receive the acceleration measurements and the electrocardiogram measurements via wireless communications from one or more sensor modules connected to the one or more accelerometers and the plurality of electrodes.

7. The system of claim 1, comprising a defibrillator, and in which the processing apparatus is configured to:
activate the defibrillator responsive to the determination of the cardiac condition.

8. The system of claim 1, in which the cardiac condition is ventricular fibrillation or supraventricular tachycardia.

9. The system of claim 1, in which the machine learning module is a first machine learning model, and in which the processing apparatus is configured to:
input features extracted from the acceleration measurements to a second machine learning module that has been determined based on training data; and
determine the posture pattern based on output of the second machine learning module.

10. The system of claim 9, in which the posture pattern is selected from a set of posture patterns that comprises sitting, standing, walking, running, lying, and fallen.

11. The system of claim 9, in which the processing apparatus is configured to:
determine a feature based on an estimate of an entropy of a normalized power spectral density of a sequence of the acceleration measurements; and
determine the posture pattern based in part on the feature.

12. The system of claim 9, in which the processing apparatus is configured to:
determine a feature based on an estimate of a power spectral density within a frequency band for a sequence of the acceleration measurements; and
determine the posture pattern based in part on the feature.

13. The system of claim 1, in which the processing apparatus is configured to:
determine a feature based on an estimate of an entropy of a normalized power spectral density of a sequence of the acceleration measurements; and
determine the cardiac condition based in part on the feature.

14. The system of claim 1, in which the processing apparatus is configured to:
determine a feature based on an estimate of a power spectral density within a frequency band for a sequence of the acceleration measurements; and
determine the cardiac condition based in part on the feature.

15. The system of claim 1, in which the processing apparatus is configured to:
determine a feature based on an estimate of an entropy of a normalized power spectral density of a sequence of the electrocardiogram measurements; and
determine the cardiac condition based in part on the feature.

16. The system of claim 1, in which the processing apparatus is configured to:
determine a feature based on an estimate of a power spectral density within a frequency band for a sequence of the electrocardiogram measurements; and
determine the cardiac condition based in part on the feature.

17. The system of claim 1, in which the processing apparatus is configured to collect training data with the garment, and in which some of the training data has been gathered from the human using the garment.

18. The system of claim 1, in which the processing apparatus is configured to:
determine a profile of the human including a plurality of features based on the electrocardiogram measurements;
compare the profile to a registered template associated with an identity;
confirm the identity of the human based on comparison of the profile to the registered template; and
transmit or display information about the confirmed identity along with the alert message that indicates the determined cardiac condition.

19. A method comprising:
receiving acceleration measurements from one or more accelerometers of a garment worn by a human;
receiving electrocardiogram measurements from electrodes of a garment worn by the human;
determining a posture pattern of the human based on the acceleration measurements;
determining a cardiac condition of the human based on the posture pattern and the electrocardiogram measurements by inputting features extracted from the electrocardiogram measurements and the posture pattern to a machine learning model previously determined based on training data; and
transmitting or displaying an alert message that indicates the determined cardiac condition.

20. A system comprising:
a processor;
a network interface; and
a memory storing instructions executable by the processor that upon execution by the processor cause the processor to perform operations comprising:
receiving acceleration measurements from one or more accelerometers of a garment worn by a human;
receiving electrocardiogram measurements from electrodes of a garment worn by the human;
determining a posture pattern of the human based on the acceleration measurements;
determining a cardiac condition of the human based on the posture pattern and the electrocardiogram measurements by inputting features extracted from the electrocardiogram measurements and the posture pattern to a machine learning model previously determined based on training data; and
transmitting, via the network interface, an alert message that indicates the determined cardiac condition.

* * * * *